(12) United States Patent
Hansen et al.

(10) Patent No.: US 11,355,808 B2
(45) Date of Patent: Jun. 7, 2022

(54) POWER SOURCE FOR PORTABLE MEDICAL DEVICES

(71) Applicant: Turner Imaging Systems, Inc., Orem, UT (US)

(72) Inventors: Douglas P. Hansen, Spanish Fork, UT (US); Keith Decker, Pleasant Grove, UT (US); Jacob Cassinat, Provo, UT (US)

(73) Assignee: Turner Imaging Systems, Inc., Orem, UT (US)

( * ) Notice: Subject to any disclaimer, the term of this patent is extended or adjusted under 35 U.S.C. 154(b) by 188 days.

(21) Appl. No.: 16/778,715

(22) Filed: Jan. 31, 2020

(65) Prior Publication Data

US 2021/0184187 A1 Jun. 17, 2021

Related U.S. Application Data

(60) Provisional application No. 62/948,685, filed on Dec. 16, 2019.

(51) Int. Cl.
*H05G 1/10* (2006.01)
*H01M 50/20* (2021.01)
(Continued)

(52) U.S. Cl.
CPC ............. *H01M 50/20* (2021.01); *A61B 6/40* (2013.01); *A61B 6/42* (2013.01); *A61B 6/4405* (2013.01);
(Continued)

(58) Field of Classification Search
CPC .......... A61B 6/40; A61B 6/42; A61B 6/4233; A61B 6/4405; A61B 6/4441; A61B 6/56; A61B 2503/10; A61B 2562/0209; A61B 5/1118; A61B 5/296; A61B 5/6804; A61B 2560/0223; A61B 2562/18; A61B 5/0004; A61B 5/0015; A61B 5/0022; A61B 5/02055; A61B 5/30; A61B 5/318; A61B 5/369; A61B 5/389; A61B 5/6805;
(Continued)

(56) References Cited

U.S. PATENT DOCUMENTS 5,721,482 A 2/1998 Benvegar et al.
7,224,769 B2 5/2007 Turner
(Continued)

FOREIGN PATENT DOCUMENTS

WO 2019161385 A1 8/2019

OTHER PUBLICATIONS

Kodak Piont-of-Care CR-ITX 560 System, Mobile X-ray and CR integration at an affordable price, Carestream Health, Inc. 2007. Brochure, pp. 4.

*Primary Examiner* — Irakli Kiknadze
(74) *Attorney, Agent, or Firm* — Kenneth E. Horton; Barnes & Thornburg LLP (57) ABSTRACT

This application describes an internal, re-chargeable power source for a portable medical device. The power source contains a removable battery pack comprising a lithium-containing material with 5 to 7 battery cells in series, each individual cell having a current capacity ranging from about 3000 mAh to about 3700 mAh. The power source can have a total energy capacity ranging from about 65 Watt-hour to about 170 Watt-hours. Other embodiments are described.

17 Claims, 6 Drawing Sheets

(51) Int. Cl.
*H01M 10/0525* (2010.01)
*H01M 4/58* (2010.01)
*A61B 6/00* (2006.01)

(52) U.S. Cl.
CPC .............. *A61B 6/4441* (2013.01); *A61B 6/56* (2013.01); *H01M 4/5825* (2013.01); *H01M 10/0525* (2013.01); *H01M 2220/30* (2013.01)

(58) Field of Classification Search
CPC ....... A61B 5/6841; A61B 6/032; A61B 6/035; A61B 6/4014; A61B 6/4028; A61B 6/4085; A61B 6/4266; A61B 6/4435; A61B 6/4476; A61B 6/4482; A61B 6/466; A61B 6/481; A61B 6/485; A61B 6/486; A61B 6/504; A61B 6/5235; A61B 6/548; A61B 6/037; A61B 2562/0219; A61B 2562/04; A61B 2562/125; A61B 2562/164; A61B 5/002; A61B 5/0205; A61B 5/112; A61B 5/6802; A61B 6/04; A61B 6/547; A61B 6/4452; A61B 6/027; A61B 6/02; A61B 6/5211; A61B 6/4411; A61B 6/4225; A61B 6/462; A61B 6/0407; A61B 46/40; A61B 6/4423; A61B 46/10; H01M 10/0525; H01M 2220/30; H01M 4/5825; H01M 50/20; H01M 50/247; G16H 40/67; G16H 10/60; G16H 10/65; G16H 40/63; G16H 20/30; H02K 11/0094; H01G 11/24; H01G 11/26; H01G 11/32; H01G 11/36; H01G 11/38; H01G 11/46; H01G 11/86; H01G 11/48; H01G 11/50; Y02E 60/10; A61N 5/10; G21F 9/001; G21F 3/00
USPC ........................................................ 378/102
See application file for complete search history.

(56) References Cited

U.S. PATENT DOCUMENTS

| | | |
|---|---|---|
| 7,496,178 B2 | 2/2009 | Turner |
| 9,194,828 B2 | 11/2015 | Turner |
| 9,442,083 B2 | 9/2016 | Turner et al. |
| 2003/0230303 A1 | 12/2003 | Nichols et al. |
| 2007/0253540 A1* | 11/2007 | Anderton ................. H05G 1/24 378/199 |
| 2008/0092043 A1* | 4/2008 | Trethewey .............. G06F 3/038 715/705 |
| 2009/0193160 A1 | 7/2009 | Kagawa |
| 2017/0027532 A1 | 2/2017 | Joshi et al. |
| 2018/0108447 A1 | 4/2018 | Turner et al. |
| 2018/0317870 A1* | 11/2018 | Fehre ................... A61B 6/4405 |
| 2019/0015057 A1* | 1/2019 | Diaz Carmena ..... A61B 6/4405 |
| 2020/0345318 A1 | 11/2020 | Turner et al. |

* cited by examiner

POWER SOURCE FOR PORTABLE MEDICAL DEVICES

CROSS-REFERENCE TO RELATED APPLICATION

This patent application claims priority of U.S. Provisional Application Ser. No. 62/948,685, filed on Dec. 16, 2019, the entire disclosure of which is hereby incorporated by reference.

FIELD

This application relates generally to portable medical equipment. More specifically, this application relates to power sources that can be used with portable medical equipment, especially portable x-ray imaging devices.

BACKGROUND

X-ray imaging systems typically contain an X-ray source and an X-ray detector. The X-ray detector is often an image intensifier or even a flat panel digital detector. X-ray imaging systems are often configured as a C-arm assembly with the source and detector on opposite ends of the "C" arm. The C-arm assembly can move through continuous rotation angles relative to the object in order to acquire images from multiple orientations.

Medical X-ray imaging equipment, especially when configured as a C-arm, is traditionally heavy and cumbersome to move and position in order to obtain the desired patient images within the operating room environment. Because the equipment is heavy, and draws significant electrical power, it has not been possible to make the devices light enough and small enough to be portable, and hand-held (i.e., hand-carried, and/or hand-operated). Advances in many technologies associated with X-ray systems are changing this situation and opening up new applications and much greater ease of use than before. These new applications and greatly improved ease of use require an internal power source, a battery, in order to obtain the maximum ease of use and opening up new operating modes and applications for x-ray imaging systems that are portable or hand-held.

SUMMARY

This application relates generally to power sources that can be used with portable medical equipment, especially portable x-ray imaging devices. In particular, this application describes an internal, re-chargeable power source for a portable medical device. The power source contains a removable battery pack comprising a lithium-containing material with 5 to 7 battery cells in series, each individual cell having a current capacity ranging from about 3000 mAh to about 3700 mAh. The power source can have a total energy capacity ranging from about 65 Watt-hour to about 170 Watt-hours. The internal power source can support a high power demand for a few moments, followed by a long time with lower power but with a rapid wake-up capability, combined with the ability to sustain operation of the portable x-ray device for a significant number of hours.

BRIEF DESCRIPTION OF THE DRAWINGS

The following description can be better understood in light of the Figures which show various embodiments and configurations of the power sources and associated methods that can be used with portable medical devices.

Together with the following description, the Figures demonstrate and explain the principles of the structures, methods, and principles described herein. In the drawings, the thickness and size of components may be exaggerated or otherwise modified for clarity. The same reference numerals in different drawings represent the same element, and thus their descriptions will not be repeated. Furthermore, well-known structures, materials, or operations are not shown or described in detail to avoid obscuring aspects of the described devices.

DETAILED DESCRIPTION

The following description supplies specific details in order to provide a thorough understanding. Nevertheless, the skilled artisan will understand that the described power supplies, batteries, battery cell configurations, minimum and maximum power constraints, and weight and size considerations and trade-offs, and power and energy use and management techniques can be implemented and used without employing these specific details. Indeed, the described systems and methods for controlling the power and energy use in X-ray devices and displaying images and video obtained by these devices can be placed into practice by modifying the described systems and methods and can be used in conjunction with any other imaging apparatus or imaging techniques. For example, while the description below focuses on internal, interchangeable power supplies and batteries used with C-arm x-ray devices, they can be used with other X-ray imaging arms and x-ray devices, including U-arms or portable x-ray devices with separate detectors that are configured to approximate the C-arm configuration. In addition to X-ray imaging, the methods described herein may be employed with any portable medical device that needs a high power demand for a few moments, followed by a long time with lower power but with a rapid wake-up. Examples of such portable medical devices include ultrasound and/or nuclear magnetic resonance (NMR) imaging systems.

In addition, as the terms on, disposed on, attached to, connected to, or coupled to, etc. are used herein, one object (e.g., a material, element, structure, member, etc.) can be on, disposed on, attached to, connected to, or coupled to another object—regardless of whether the one object is directly on, attached, connected, or coupled to the other object or whether there are one or more intervening objects between the one object and the other object. Also, directions (e.g., on top of, below, above, top, bottom, side, up, down, under, over, upper, lower, lateral, orbital, horizontal, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

Figure 1A:
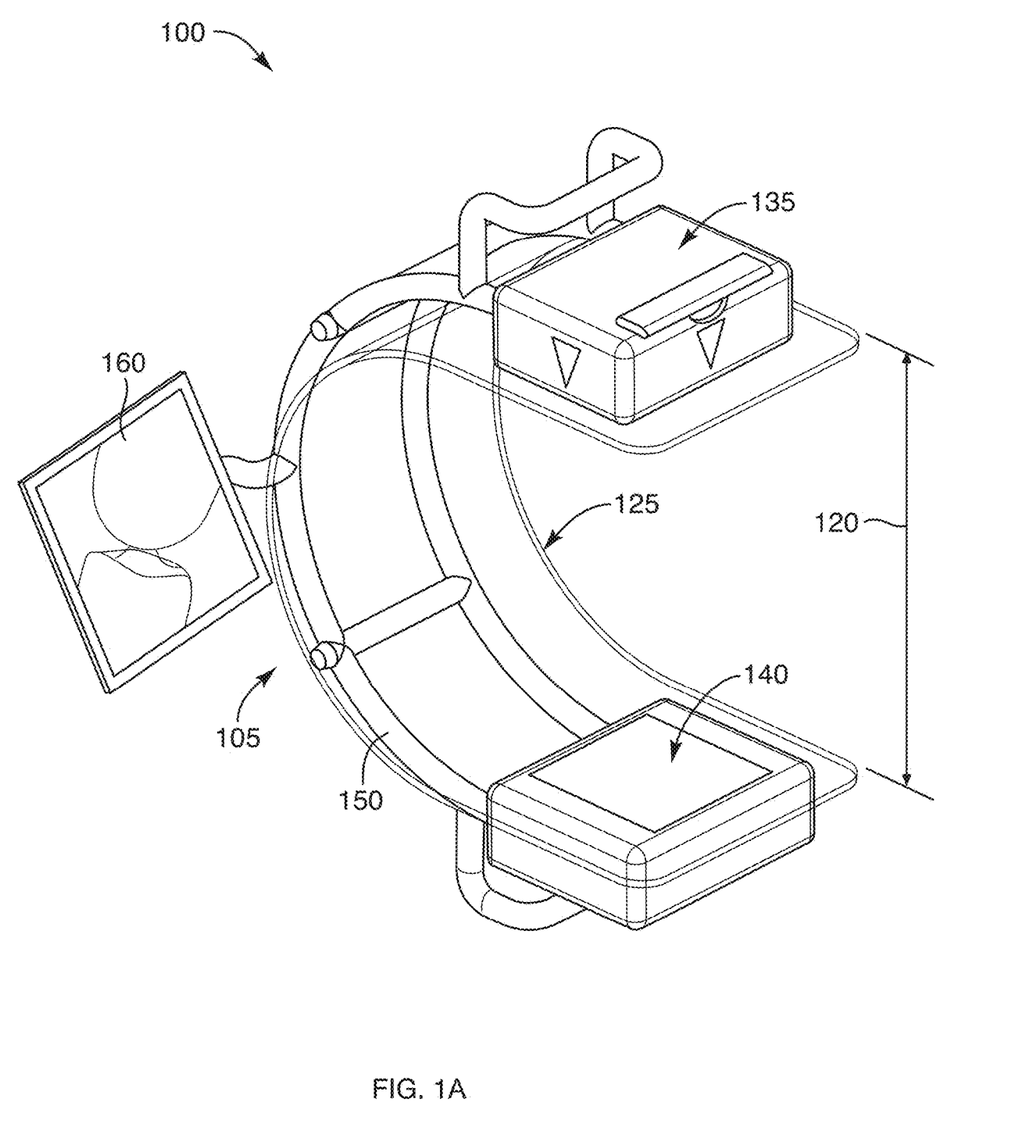
FIGS. 1A and 1B shows a view of some embodiments of small, hand-held X-ray devices.
Figure 1B:
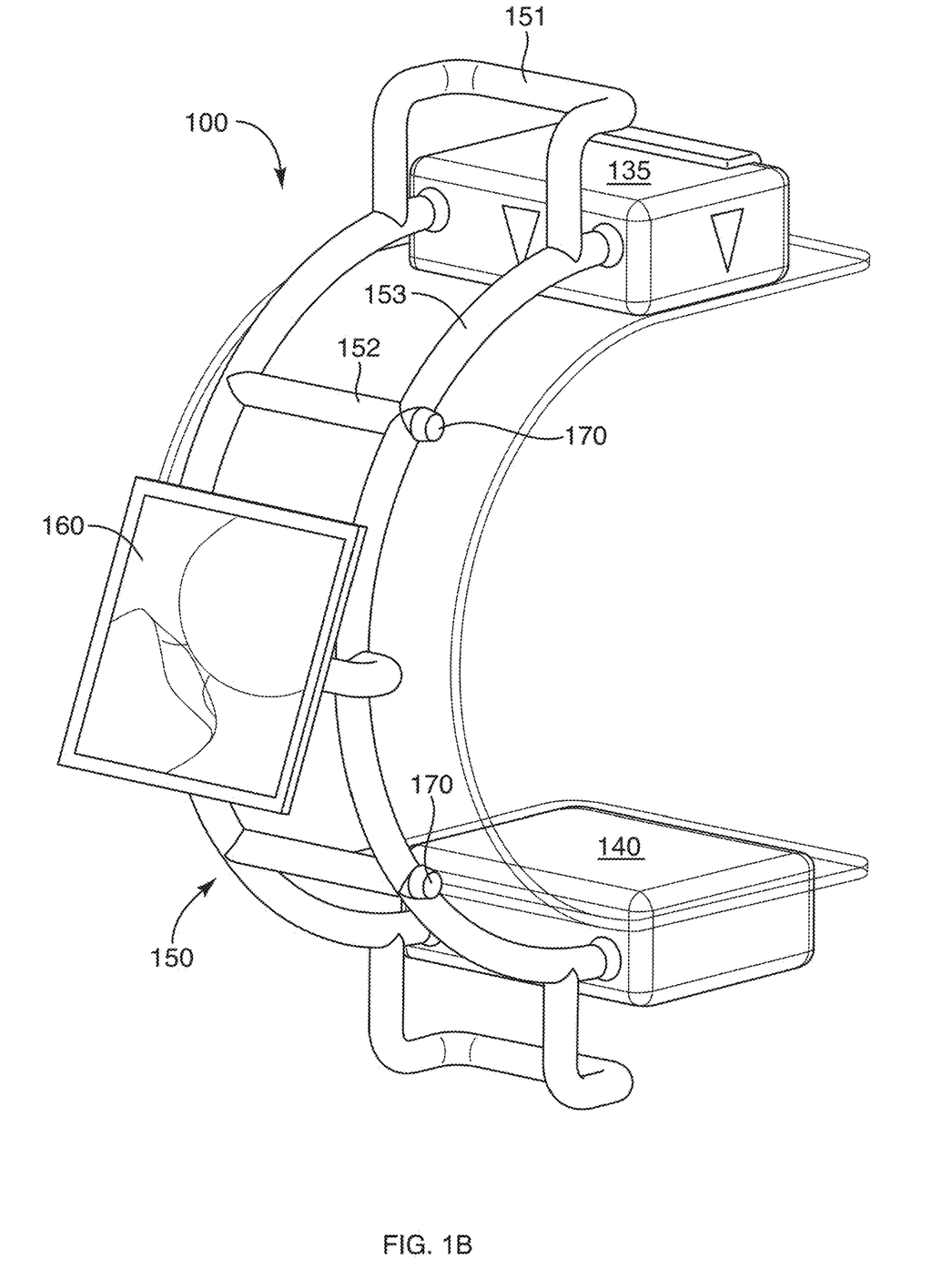

The figures show some embodiments of the portable medical devices and internal powers sources that can be used with such devices. As shown in FIGS. 1A and 1B, the portable medical device can include X-ray devices (or an x-ray system) 100 containing an imaging arm (or support arm) that allows the system to be used to take X-ray images of a portion of a patient's body or any other object capable of being analyzed by x-rays, including animals, industrial components such as electronic circuit boards, containers to be inspected, and/or passenger luggage. In some configurations, the imaging arm is substantially shaped like the letter "C" and is therefore referred to as a C-shaped support arm (or C-arm) 105. The C-arm can have any size that can be held and operated by hand when in use, as seen in FIG. 1A or 1B. The x-ray devices 100 are hand-held so that they can be carried by hand and/or operated by hand.

The C-arm 105 can contain any X-ray source 135 and X-ray detector 140 that allow the X-ray device 100 to take X-ray images. The X-ray source 135 can contain any source that generates and emits X-rays, including a standard stationary anode X-ray source, a micro-focus x-ray source, a rotating anode x-ray source, and/or a fluoroscopic X-ray source. In some embodiments, the x-ray source 135 can operate with about 40 to about 90 kV and from about 1 to about 10 mA. In other embodiments, the x-ray source can operate with about 70 KV to about 120 KV and from 1 to about 15 mA. In still other embodiments, the x-ray source can operate with about 75 kV and about 2 mA. In some configurations, the X-ray source and x-ray detector can be made modular so that different sizes and types of X-ray sources and x-ray detectors can be used in the x-ray device 100.

The X-ray detector 140 can contain any detector that detects X-rays, including an image intensifier, a CMOS camera and/or a digital flat panel detector. In some configurations, the detector can have a substantially square shape with a length ranging from about 13 cm to about 15 cm, about 17 cm, or even about 20 cm. In other configurations, though, the x-ray detector 140 does not need to have a substantially square shape. In addition, the x-ray detector can have a pixel size that ranges from a square with dimension ranging from about 25 µm to about 200 µm, to a rectangle with the two dimensions of the rectangular pixel fitting in about the same range.

Figure 2:
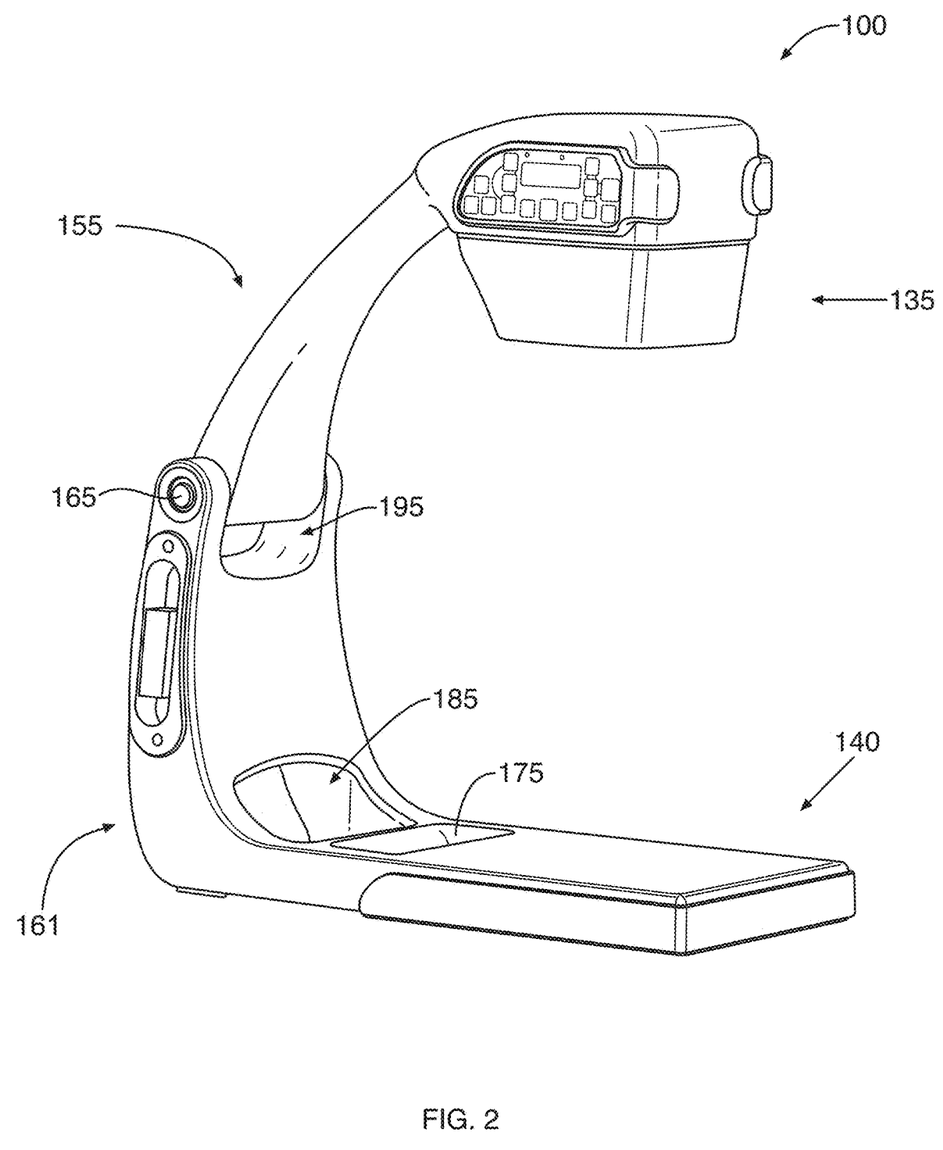
FIG. 2 shows another view of some embodiments of small, hand-held X-ray devices.

In other configurations, the detector can have a substantially rectangular shape with the shorter dimension ranging from 12 cm to 16 cm, and the longer dimension ranging from about 18 cm to about 24 cm. The X-ray source 135 can be contained in a housing that can be configured in two parts with a first part 155 enclosing the x-ray source 135 and a second, separate part 161 enclosing the x-ray detector 140, as shown in FIG. 2. In other configurations, however, the housing can be configured so that it is a single part that encloses both the X-ray source 135 and the X-ray detector 140.

In some configurations, the housing can also enclose a removable power source (such as a battery) and optionally an internal power supply. Thus, the power source and the power supply can be located internal to the housing and also to the x-ray device 100. The supporting electronics for the power source and the power supply, as well as the supporting electronics for an image display and for wireless data upload, can also be located internal to the housing. Thus, in these configurations, the x-ray device 100 does not contain an external power cord or data cable. Incorporating the removable power source (i.e., the battery), the power supply, and the supporting electronics all within the housing simplifies the system for easier use, and allows the size and the weight of the device 100 to be reduced. With such a configuration, the power source can easily be replaced and delivers 60, 80, 100, 120, or even more x-ray images using just a single charge, with the exact number of images obtained with a single power source depending on the voltage and current parameters required for the images taken with a higher power setting reducing the number of images that can be obtained. Of course, if needed, the x-ray device 100 can be configured so that it is alternately, or additionally, charged using external power from a power cord that is plugged into a wall outlet. In other configurations, multiple power supplies can be provided for the source, detector, and control electronics, any (or all) of which can be located either internal or external to the housing.

In some instances, the X-ray device 100 contains a frame 150 that has an open configuration. As shown in FIGS. 1A and 1B, an open configuration gives a number of easy gripping options for a user to carry and hold the frame 150 during transport, and optionally during operation of the x-ray device 100. In some embodiments, the frame 150 can be configured as a modular unit so different cross members (or length member or handles) can be used to replace the existing cross members (or length member or handles). Thus, the frame 150 provides the ability for a user (or operator) to grip and hold the X-ray device 100 during operation, a feature that is useful since some other conventional C-arms can't be held in the hands while being operated because they do not have a suitable frame and because they are too heavy.

The X-ray device 100 can also contain an optional shield 125. The shield 125 is used to protect a user from backscattered x-rays when the device 100 is operated. The shield 125 can accordingly be made of any radiation shielding material (including a leaded acrylic material) and shaped so that it protects the user. The shield 125 can be configured to be removed from the x-way device 100, if needed.

The X-ray device 100 can also contain a user input/output (I/O) mechanism. In some embodiments, the I/O mechanism contains a user interface and a display that is combined in a touchscreen monitor 160, as shown as shown in FIGS. 1A and 1B. The monitor 160 can be positioned in a first orientation (as shown in FIG. 1A), in a second orientation (as shown in FIG. 1B), or any other desired position. In other configurations the x-ray device is merely connected to the I/O mechanism.

The x-ray device 100 can be activated by a trigger located anywhere on the x-ray device 100 that can be activated easily by the user. For example, the trigger could be activated near locations 151, 152, 153, and/or 170 on the C-arm. In other configurations, a separate foot switch that communicates with the x-ray device 100 using a wired or Bluetooth/ wireless connection can be used. Indeed, the portable x-ray device 100 could be equipped with both a trigger on the device as well as a foot switch. In this manner, the surgeon, radiologist, medical practitioner, or other user can simultaneously control the manner in which the x-ray images are obtained by holding or guiding the x-ray device 100 while viewing the results obtained from the imaging on a conveniently-located display. This is one of the features enabled by the x-ray device 100. The ability to easily guide or manipulate the x-ray device 100 by hand while simultaneously viewing the image results enables the medical practitioner to obtain the x-ray images or video information needed to support the desired medical procedure in a manner similar to the way digital still and video cameras in cell phones and other personal electronic devices have enabled new and more effective ways to document, communicate, use, and share visual information. These configurations thus enable quicker and better medical decisions and encourage more frequent imaging "snapshots" during medical procedures which will lead to medical practitioners acting on better information, with the final result being better medical outcomes for the patient.

In other embodiments, the portable x-ray device 100 has the configuration illustrated in FIG. 2 where the frame has a first portion 155 that is part of the housing that contains the x-ray source 135 and the associated electronics. The frame also has a second portion 161 that is part of the housing that also contains the x-ray detector 140 and the associated electronics. The first portion 155 of the housing and the second portion 161 of the housing are connected using hinge 165 within opening 195. The bottom of the portable x-ray device can contain an opening 175 and/or opening 185 that can be used when attaching the x-ray device 100 to an external support structure.

The portable x-ray device 100 has several features not exhibited by other C-arm devices. First, it has the capability of wireless data transfer, thereby eliminating the need for any wired connections or cables to the C-arm 105 or imaging arm. Second, it is internally powered by a removable battery or internal power source and, therefore, more portable than other C-arm devices that require a power cable. Third, it is lighter than other C-arm devices. As a comparison, the portable x-ray devices 100 described herein can have a weight ranging from about 10 to about 25 pounds while other C-arm devices have a weight ranging from about 35 to about 375 pounds. In other embodiments, the portable x-ray C-arm devices 100 described herein can have a weight ranging from about 12 to about 18 pounds.

The x-ray device 100 can also be connected to any type of electronic device with a wireless or a wired connection. In these embodiments, the portable x-ray device 100 itself can analyze, process, and/or transmit image or video data to the desired electronic device, (such as a desktop computer, laptop computer, tablet, cellphone, etc. . . . ), which can be used to view the x-ray images and, in some configurations, further analyze the x-ray images from the x-ray detector. These operations (image compression/decompression, brightness adjustment, metal detection, and other types of image analysis typically performed an x-ray image data) can be triggered by any one of the triggers and/or the foot switch contained within the x-ray device 100. In other embodiments, however, the x-ray detector 140 can be connected, or paired, with any wireless communications device that can be paired with the desired electronic device, such as a tablet, display monitor, etc.

The portable x-ray devices and methods for imaging described herein exhibit several useful features. Among these features is the capability for Wi-Fi communications, image compression, and other exposure control and image quality improvement techniques that are helpful to the operator when using the portable x-ray devices for x-ray imaging. These features simplify use and make medical images faster and easier to obtain.

Figure 3:
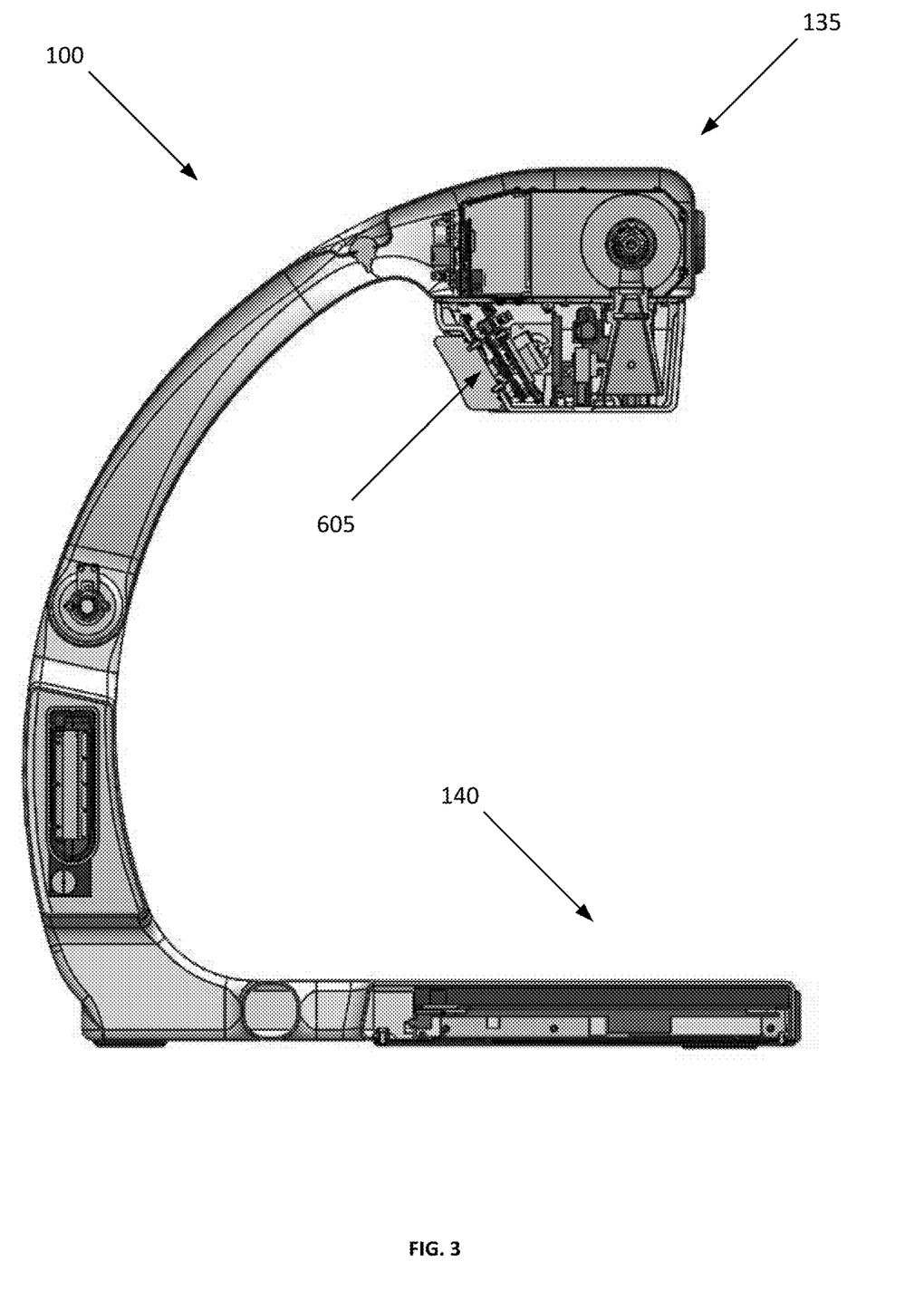
FIG. 3 shows some embodiments of small, portable X-ray devices containing an internal power source.

As described herein, the x-ray device contains a lightweight internal power source. In some configurations, a lightweight but powerful power source 605 (i.e., a battery pack) can be mounted internally, as shown in FIG. 3. Mounting the power supply internally, rather than as a separate battery pack attached to a belt worn by user, or as otherwise mounted or carried in some fashion external to the device, again makes the portable x-ray device easier to manipulate and use. This battery pack (or similar internal power source) can be combined with a power management module, either in the battery pack, or as a separate component in the x-ray device 100. The power management module helps manage the power provided by the battery pack to optimize the battery pack and the system energy efficiency for the x-ray device or other portable medical device.

Optimizing the system energy efficiency helps to effectively operate the portable x-ray imaging device. Obtaining sufficient operational life from a single battery charge can be helpful during the successful operation of the portable x-ray imaging system. The power source or battery must be able to deliver sufficient energy (typically measured in watt-hours, kilowatt-hours, or other equivalent measures such as amp-hours or milliamp-hours), to enable use of the device throughout at least one medical procedure. Most medical procedures can take an hour or more to complete. It is helpful that the energy provided by the battery pack (or other internal power source) be sufficient to cover multiple procedures with an adequate reserve capacity so that there is little concern that the imaging system may run out of power if the medical procedure most be prolonged due to unforeseen problems or complications.

An example of the amount of energy used during a typical medical procedure can be determined by considering a typical x-ray imaging use pattern. A typical medical procedure using the x-ray device 100 could be expected to last about one hour. During this hour, the device will be used in active x-ray image acquisition for up to about two minutes, or about 120 seconds. However, these two minutes of use will typically occur as a number of imaging sequences lasting anywhere from a few seconds up to about 10 to about 15 seconds for each sequence. These imaging sequences occur near the beginning of the procedure, during the procedure, and at the end of the procedure in a manner that may not be predictable in advance. Therefore, it is not practical to use the x-ray imaging system for a certain short period of time and then turn it off to preserve the battery charge. The imaging device must always be ready for use within seconds after the surgeon indicates that he or she needs to obtain a set of x-ray images. So the imaging device often needs to operate in a lower-power "stand-by" mode while waiting for the next imaging sequence to be taken.

Operation in a stand-by mode is common among computers and many other types of information technology (IT) equipment, including cell phones, televisions, and other devices. Most of these devices can "wake-up" and be ready to operate within a few seconds after they are reactivated. However, such systems do not have the challenging operational requirements of portable medical devices, and in particular, an x-ray imaging device or system. An x-ray imaging system needs to first activate the x-ray source, which has a particular need for the filament to heat up so that it can emit electrons and cause the x-ray source to emit x-rays. The system also activates the x-ray detector and its associated microprocessor and data-handling electronics, both of which can take some time to return to a ready state, depending on how "deep" the sleep state is. Therefore, the depth of the "sleep" or the "stand by" state must be such that these devices can return to operation within a few seconds of receiving the reactivation signal. In particular, the entire system must be ready to generate an image sequence within a time of about 1, about 2, about 3, about 4 seconds, 5 seconds, or perhaps as long as about 8, about 10, or about 15 seconds, including any sub-range or combination of these times, after the reactivation signal is initiated, with the shorter activation times being preferred.

This rapid reactivation can also guide the choice of the components that are used in the x-ray imaging device. In some embodiments of the x-ray device 100, there are at least 6 subsystems that work together in order for the x-ray device to function properly and to reactivate quickly and without error. These subsystems are (1) the control system or core CPU, (2) the image processing FPGA card, which works closely with the (3) x-ray detector, (4) the wireless access point, (5) the battery or power source, and (6) the x-ray source. These subsystems can coordinate and work with one another to ensure that the x-ray source is only active when desired and when the x-ray detector and other components are ready to receive x-ray radiation and obtain proper x-ray images. Exposure of a patient, users, or by-standers to x-ray radiation by accident, or by an attempt to take an x-ray image when the detector and other system components are not ready can cause the patient to receive a radiation dose for no countervailing medical benefit, and therefore must be prevented or minimized. Accordingly, the various subsystems should communicate with one another to prevent improper x-ray exposure and to coordinate the image gathering, image analysis, and image data transmission process.

The image generation process illustrates the desired communication, and the unique challenges, of reactivating the x-ray imaging device from a sleep mode. To generate an x-ray image that is displayed for the surgeon or other medical professional, the device is activated by the operator pressing one of the buttons on the x-ray device or a footswitch pedal that is connected to the x-ray device wirelessly or by a wired connection. This activation triggers the control system or system computer to notify the detector, the FPGA, and the x-ray source that an x-ray image is required. The x-ray source requires less than a second to prepare to fire the first x-rays, after which it can repeat at a rate of 10 or more x-ray pulses per second. Once the x-ray source is ready, the control system checks that the detector and FPGA are in an enabled state and ready to capture the image. If all system components are ready, then the control system triggers the x-ray pulse, the detector captures the image, the FPGA processes the image data to remove noise, correct for a flat dark field image, dead pixels, and/or provide other image enhancements or corrections. Then the image data is passed to the wireless access point for transmission to the associated electronic device (i.e., a tablet computer) where the x-ray image is displayed. To support this operation without using excess energy from the battery, the control system and battery must deliver power at a high rate during the image generation sequence and then return the system power demand quickly back to a lower power state.

All of this communication between subsystems takes place on a communications pathway (or bus) shared by all of the subsystem components. This communications bus can be any high-speed communications pathway such as a PCIE bus, an Ethernet-protocol network, USB network, or other common system data network. The communications between the various subsystem components can be controlled by a system controller or system computer that can be any type of micro-controller or computer such as a Raspberry Pie machine, a computer based on Microsoft Windows using Intel or AMD CPUs, a computer based on Linux, another type of microcontroller, and/or an FPGA-based processor. The choice of computer can be made based on its intrinsic power needs, its processing power, the processing power required to control the system and manage the data flowing from the detector, and similar considerations.

In some configurations, neither the system controller nor the communications bus directly control the power demand in the x-ray device 100. Rather, the power draw on the battery (or other internal power) can be determined by the activity state of all the various subsystems at any particular moment. The system controller determines the power that needs to be drawn from the battery moment by moment and synchronizes and/or coordinates the subsystem activities according to the control algorithms and control software that have been programmed into the system computer. Therefore, the power drain and power usage can be controlled indirectly in these configurations by coordinating the system operations, not by controlling the battery.

When the x-ray system is activated and operating, the management of this communications pathway or bus is straightforward. However, when the x-ray system transitions from an active to a sleep state, and then back again, this communications pathway should be managed to make sure that the subsystems are activated in the proper sequence and timing in order to avoid operational errors that might cause the system to malfunction. For example, some components or subsystems (such as the control system or internal computer) can enter an error state if they detect a problem with the communications bus. Such errors can occur because one subsystem may need to exchange information with a second subsystem, and if that second subsystem is not active and therefore does not respond, the first subsystem may report an error state. Other types of communication problems can also occur that are related to the timing of signals and the activation of various subsystems. Therefore, some subsystems (or components therein) should activate before other subsystems, requiring that deactivation and activation must be scripted and controlled carefully through the system controller and the associated algorithms and software so that no errors are generated during the transition process. While some embodiments may require a certain activation sequence, other embodiments (with different subsystem components reflecting different design choices) may require a different sequence or control algorithm.

There are still other considerations which determine which subsystems (and/or components of the subsystems) are "put to sleep" and are temporarily not active and which are allowed to remain active. The system controller or CPU can typically be one of the most power-hungry components, even when care is taken to use a low-power component. For example, a typical low-power CPU can still require about 3 watts, about 4 watts, about 5 watts, about 6 watts, about 8 watts, or even more when operating, even on the lowest power setting or sleep mode. Accordingly, it can be helpful to keep that component in the "sleep" mode whenever possible. Of course, if the system CPU is in a "sleep" mode, care must be taken to ensure that the other subsystem components are either put into a quiescent state before the CPU, or that they are able to operate in at least a semi-autonomous mode when the system controller or CPU is "sleeping."

An example of one such component is the wireless access point that maintains WiFi communications with the external components such as the tablet computer and display. The WiFi access point can require significantly less power than the CPU and, therefore, may be allowed to remain substantially active the entire time the x-ray device operates. In many embodiments, it can advantageous to leave the wireless access point active because maintaining the wireless link or WiFi with the electronic device (i.e., tablet) at substantially all times can be helpful to maintain safe system operation. Therefore, a wireless access point can be chosen to provide both high data transmission rates (compliant with IEEE802.11n, IEEE 801.11ac, or a faster Wi-Fi protocol) and a low power demand. Appropriate power levels for the wireless access point could be about 0.5 watts or less, about 1.0 watts or less, about 2.0 watts or less, and even up to a maximum continuous power demand of about 5 watts. Another subsystem that can remain in the active mode is the wireless link (Bluetooth or similar wireless data communications protocol) with the foot switch so that the foot switch will always be available and active during the procedure, whether or not the x-ray imaging system is active or in a low-power mode. Both the tablet wireless link and the footswitch wireless link are helpful to keep in this active mode because these are two of the primary input points to the x-ray system by which the user will indicate a need to take a new set of X-ray images, or to otherwise change the operational state of the x-ray system.

Given the various operational states the x-ray imaging system can experience during operation, it can be possible to determine an acceptable battery charge capacity which properly supports the x-ray imaging system. In the configurations of the portable x-ray device 100 described herein, the energy required for about 120 seconds (two minutes) of full operation can be about 7000 Watt-Seconds, or about 1.94 Watt-hours. And during stand-by, about 18 Watts of power can be needed to maintain an acceptable activation time. Thus, about 17.4 Watt-hours of energy can be required from the battery to maintain the x-ray device 100 in the stand-by mode for about 58 minutes in the hour. Therefore, for the total hour of use, a total of about 19.346 Watt-hours of energy might be required in some configurations. To provide sufficient energy for an eight-hour work day supporting medical procedures, an available energy capacity of about 155 Watt-hours therefore might be required for operation of the x-ray device 100. In some embodiments, this energy capacity can be achieved using Lithium-ion (Li-ion), or Lithium Iron Phosphate (LiFePo) batteries, for example. Other battery configurations can be used to obtain this energy capacity, provided that the weight requirement for the portable x-ray device (or other portable medical device) is maintained.

There are other considerations in the design of hand-held x-ray imaging devices that influence the capacity needed from the internal power source. One of the advantages of a small, light-weight, hand-held x-ray imaging system like x-ray device 100 is that it can be carried onto a commercial airline flight. This device, when collapsed using the hinge 165, can fit into an overhead luggage bin in order to provide easy transport. This configuration provides a particular advantage for humanitarian missions, sports applications (where the team physician may desire to carry the imaging system with him to a distant location like a sports arena), or for other applications where it is necessary to travel by air with the x-ray imaging system. When traveling by airline, flight regulations restrict the maximum charge capacity of a battery that can be carried on to a flight to less than 100 Watt-hours. But this is less than the 155 Watt-hours capacity target that might be needed in some configurations. Reducing the energy capacity to about 100 Watt-hours, or even to about 65 Watt-hours, can be achieved by reducing the target number of useful hours per battery charge, reducing the stand-by power requirements by using lower-power components, adjusting the depth of sleep or the deactivation/reactivation sequence of the system components, turning off additional components or subsystems, or by making other adjustments in the system designed to reduce the energy required. Such other adjustments may include increasing the detector sensitivity, improving the image processing algorithms to reduce quantum noise in the displayed image (thus enabling operation with less power required from the X-ray source), and/or implementing various image averaging techniques which can accomplish a similar X-ray source power reduction. Many other adjustments may be possible depending on the system performance goals for image quality, response time, and other factors.

Other considerations that affect the battery capacity include the performance capability of the battery cells used in the assembled battery pack. Many battery cells, including Li-ion battery cells for example, come in a variety of configurations and physical sizes. Flat-pack cells are often used for fitting batteries into limited-space configurations, but cylindrical can-type cells are typically safer, more reliable, and more rugged. Cylindrical cells come in a variety of standard sizes and shapes, with diameters of about 14 mm, about 18 mm, about 21 mm, about 26 mm, and about 32 mm, and lengths ranging from 50 mm up to about 70 mm. While the larger sizes will have a larger energy capacity, the battery configuration and cell size used in the x-ray device 100 may also be selected in some configurations based upon the width and depth available for the battery within the x-ray imaging device housing and/or the weight of the larger battery sizes.

The battery voltage is also a consideration in selecting the energy capacity and battery configuration. The operational voltages provided to the system electronics by the battery (and the associated power conditioning electronics) convert the battery voltage into about 3 volts to about 5 volts, or other suitable voltage for the microcomputers, data handling circuitry, CMOS detector, and other subsystems and/or components. In the case of an x-ray imaging system such as x-ray device 100, there is also the constraint imposed by the high voltage requirements for the x-ray source. For medical x-ray imaging, the x-ray source can require a voltage ranging from about 30,000 volts (30 kV), about 40 kV, about 60 kV, about 70 kV, about 90 kV, about 120 kV or more, and/or sub-ranges or combinations of these voltages, depending on the application of the imaging system. To reach these high voltages in an energy-efficient manner using a switching power supply or other power converter, the starting battery voltage should be as high as possible. One way to achieve a higher battery voltage (and still maintain the desired battery energy capacity) is to use smaller cells in series instead of using a smaller number of larger battery cells. For a given maximum power, using a higher battery voltage reduces the maximum current requirement according to the well-known relationship that power is the voltage multiplied by the current. A smaller maximum current allows for smaller traces on circuit boards, lighter gauge (i.e., less weight) wiring harnesses, less resistive power losses, and other advantages in obtaining higher energy efficiency, and therefore lighter weight and longer battery life.

Figure 4A:
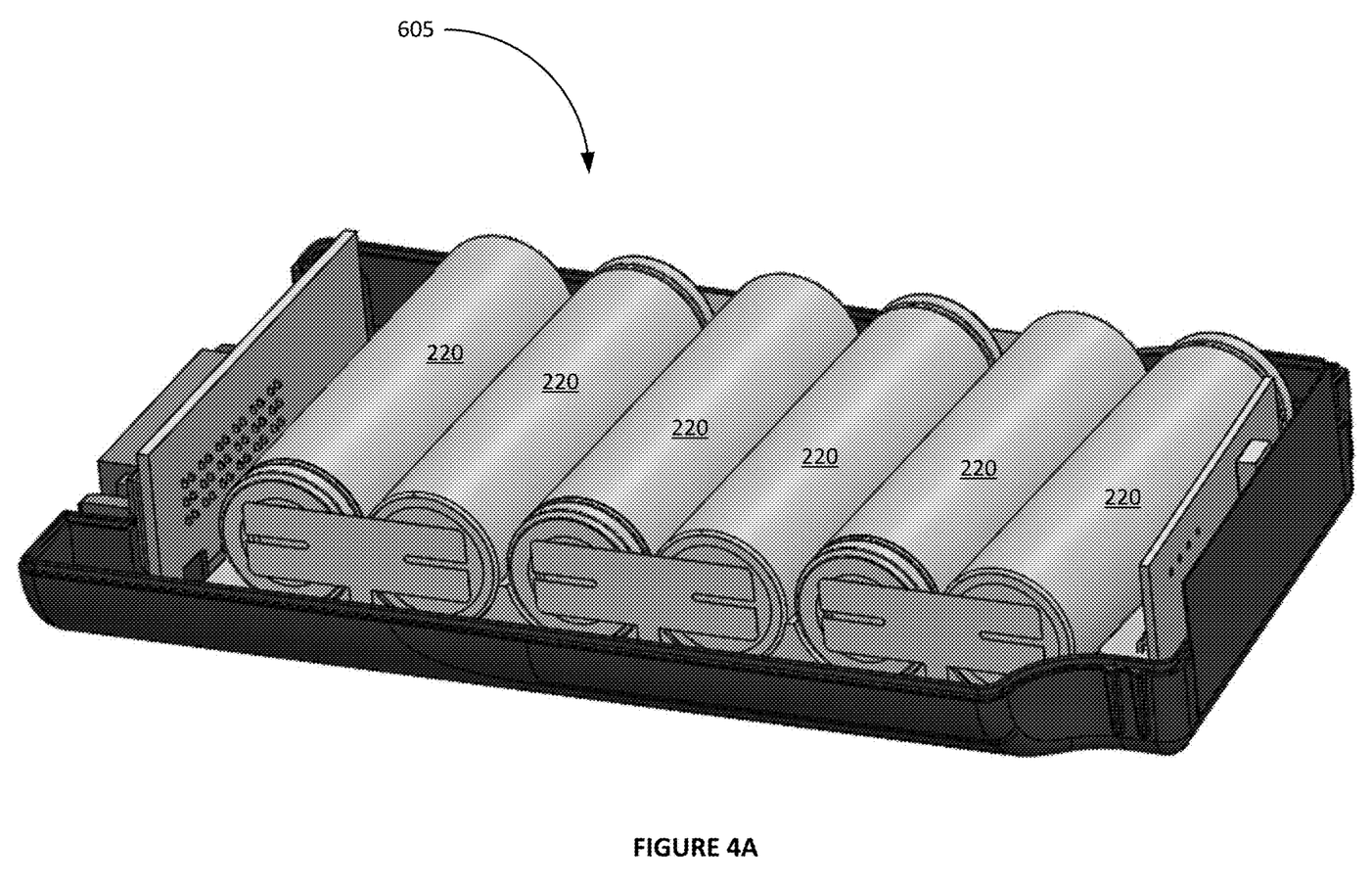
FIGS. 4A and 4B shows a close-up view of an internal battery pack that can be used with portable X-ray devices.
Figure 4B:
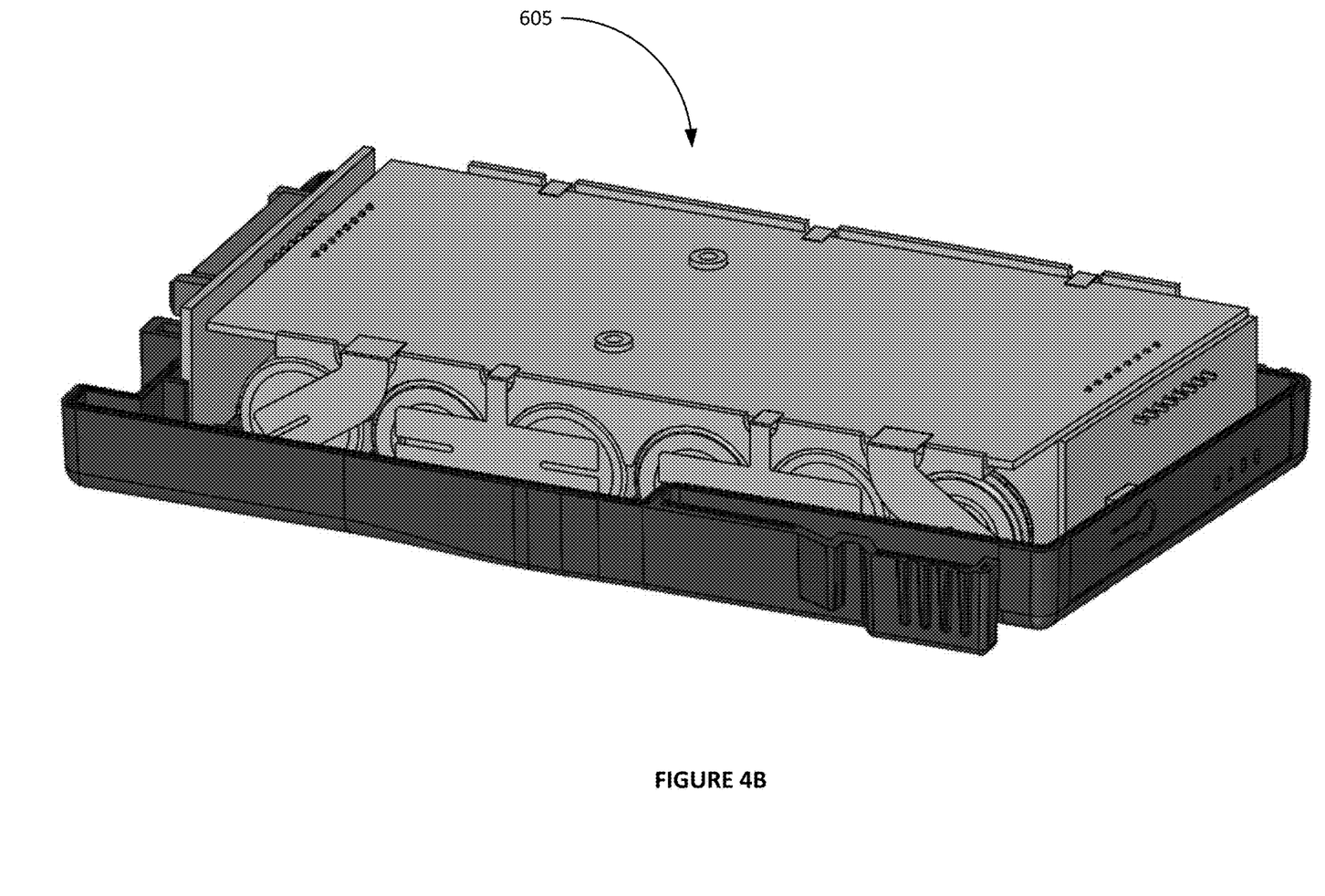

Achieving the highest battery voltage possible also strongly favors a series configuration instead of a parallel configuration for the battery cells. While the same number of battery cells in parallel provide the same theoretical energy capacity as in a series configuration, the use of that energy is more efficient with a series configuration. For illustration of this difference, a configuration with 3 cells 220 in series with 2 banks in parallel, contrary to the series configuration shown in FIGS. 4A and 4B, would give the same energy capacity as 6 cells in series, but with only half the voltage, and therefore would suffer some energy losses and additional weight in the system to compensate for the effects of the lower battery voltage.

Another consideration for the configuration of the battery pack is the cell design. Li-ion cells can be used for a variety of purposes and uses. Some uses place high current demands on the cell while others require high energy capacity. Still other uses might require some compromise between these two extremes. Li-ion cells are not currently available that provide both high current capability (i.e., currents over approximately 10 amps continuous), and high-energy capacity, so a design choice balancing between these two considerations must be used in the battery pack. In some embodiments, a higher energy capacity is selected in order to get as close as possible to the target battery capacity of 100 Watt-hours, or 155 Watt-hours, or some other desired battery capacity, while keeping the battery size and weight to a minimum by using a smaller number of cells for a given energy capacity target.

In some embodiments, Li-ion cells of about 3500 milli-amp-hours (mAh) capacity with the 18650 dimension specification can be used. In order to raise the battery voltage within the constraint of a maximum 100 Watt-hours energy capacity, 6 cells in series can be used, providing a nominal voltage of about 21.8 volts. It is also possible to use 7 cells with similar specifications and remain under the 100 Watt-hour limit. But 6 cells can be used in some embodiments to save on weight and over-all battery size in order to meet size and weight targets for the x-ray system. As well, 5 battery cells could be used but they might not provide sufficient charge storage capacity to meet a minimum acceptable operational time. Batteries of a larger size than the 18650 dimension specification were not used in these embodiments because of the weight and size constraints in the system design, but could be acceptable in other embodiments. And batteries of a smaller size than 18650 dimension specification might not be used in other embodiments due to concerns about over-all energy capacity and commercial availability.

In other configurations, though, battery cells with a current capacity of about 3200 mAh or about 3250 mAh could be used. In these configurations, 7 battery cells can be used in order to have a larger energy capacity at the cost of additional weight. Cells under about 3000 mAh capacity are not used in some embodiments of the x-ray systems because the lower energy capacity was not suitable given the combined design constraints of weight, battery size or volume, battery voltage, and energy capacity.

Another design consideration is the cell maximum sustained amperage. In some embodiments, the 3500 mAh-capacity cells were used not only because of their larger capacity, but because they were rated slightly higher in maximum sustained amperage at 10 amps versus a maximum rating of 8 amps for the alternative cells.

In some embodiments, the battery pack for the x-ray imaging system would have performance specifications within the ranges shown in Table 1. Battery voltage is not listed as a specification because the cell voltage is fixed by the choice of battery chemistry and, therefore, the cell voltage is not considered a separate or independent variable in these embodiments.

TABLE 1

Battery Performance Specifications

|  | Cell Capacity (mAh) | Cells in Series (18650 size) | Max. Current | Cell Size |
|---|---|---|---|---|
| Maximum | ~3700 mAh (determined by Li-ion chemistry | 7 | ~10 Amps | ~21700 or ~20700 |
| Minimum | ~3000 mAh | 5 | ~5 amps | ~18650 |

In other embodiments, values and/or sub-ranges within these ranges could also be used in the battery pack.

In some configurations, the battery pack can contain less or more cells. For example, the battery pack can contain 4 or 5 cells in series. In another example, the battery pack can even contain 8 cells in series provided that the 100 Wh capacity limit is not exceeded. Indeed, even more cells in the battery pack can be used provided they simultaneously meet the power, volume, energy capacity, and weight constraints. For example, instead of a 6 cell battery pack, a 12 cell battery pack could be used with half-size cells that have only half the energy capacity of a standard cell. In these configurations, the battery pack could contain two sets of 6 cells wired in series in order to get the correct voltage, with the two sets of cells connected together in parallel.

In some embodiments, the battery cells can be made from lithium-containing materials, such as the Li-Ion family of battery chemistries, lithium polymer batteries, and/or LiFePo batteries. The lithium-ion chemistry can limit the voltage to about 3.635 volts nominal on a cell and the LiFePo battery chemistry has a nominal voltage of about 3.3 volts. Other battery chemistries may be used, as long as the battery chemistry provides the performance required to meet the fundamental design constraints of weight, energy capacity, and battery size.

The considerations on individual cell energy capacity indicate that in some embodiments the preferred cell configurations (for Li-ion chemistry) are cells with the 18650, 20700 or 21700 dimension specifications. Cells with the 26500 dimension specification provide too much energy capacity per cell because at least 5 cells are needed to provide the appropriate overall cell voltage, yet 5 cells of this size are over the FAA energy limit of 100 Wh. With cells having the 18650 dimension specification, a capacity of 3 Ah is the lowest capacity per cell that can be used in a battery while maintaining sufficient energy capacity. 3.7 Ah capacity per cell (for the 18650 size) is about as high an energy capacity as the Li-Ion chemistry can currently provide.

There exists a system performance trade-off between high current capability and high energy capacity since no single battery cell design is capable of providing high performance in both specifications simultaneously. The highest current needed from the battery is the moment when the x-ray source is fired. While this high current draw is reasonably short, on the order of a few milliseconds, the current can momentarily exceed about 15 to about 20 amps. Even if the battery cells are rated to withstand these short duration high currents, such large current draws can stress the battery cell and cause more rapid deterioration of the battery and shorten its useful life. To reduce the maximum current draw, a capacitor can be used to buffer the current to provide a portion of the current surge to the x-ray source while reducing the peak current draw on the battery. In some embodiments, a capacitor of at least about 0.8 mF to about 20 mF can be used to reduce the maximum current surge to a level of about 4 amps peak to about 8 amps peak. The exact capacitance used can depend on the design of the x-ray source, the current and voltage pulse rate, and/or the pulse shape required by the x-ray source.

The portable medical devices and internal power sources described herein exhibit several useful features. Among these features is the capability to support a high power demand for a few moments, followed by a long time with lower power but with a rapid wake-up, capability, combined with the ability to sustain operation of the medical device for a significant number of hours. This capability is enabled by careful management by the portable medical device of the power from the removable, internal power source (i.e., the battery) according to the techniques and specifications described herein. To be useful in many medical procedures, the battery should provide a system operational time under normal usage of at least about 4 hours or more, about 6 hours or more, about 8 hours or more, or even about 10 hours or more, and any combination or sub-ranges of these times, before being recharged or replaced. Thus, the required energy capacity of the battery should be about 65 Watt-hours, about 100 Watt-hours, or even about 155 Watt-hours, or any amount between these numbers. Indeed, some configurations of the portable medical devices may use a higher energy capacity, the optimum configuration can be determined by the design trade-off considering factors such as weight and size of the battery and how that will affect the system design. To reduce the energy requirement of the portable medical device during operation and to allow the use of a battery of 100 Watt-hours or less, with its associated benefits in lower costs, lower weight, and relief from air-travel restrictions, several energy saving techniques can be used in the portable medical device.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A portable medical device, comprising:
   a housing, the housing including a C-shaped support arm; and
   a re-chargeable power source internal to the housing C-shaped support arm, the power source containing a removable battery pack comprising a lithium-containing material with 5 to 7 battery cells in series, each individual cell having a charge capacity ranging from about 3000 mAh to about 3700 mAh.

2. The device of claim 1, wherein the power source has a total energy capacity ranging from about 65 Watt-hour to about 170 Watt-hours.

3. The device of claim 1, wherein the battery pack comprises Li-ion or LiFePo batteries.

4. The device of claim 1, wherein the portable medical device is a portable x-ray device with a wireless data link.

5. The device of claim 4, wherein the portable x-ray device comprises:
   an X-ray source contained near one end of the support arm;
   an X-ray detector contained near the other end of the support arm.

6. The device of claim 5, wherein the X-ray device is configured to be hand-held.

7. The device of claim 6, wherein the device weighs less than about 20 pounds.

8. The device of claim 1, wherein the power source provides an operational time for the portable medical device ranging from about 6 hours to about 10 hours before being recharged or replaced.

9. A portable X-ray device, comprising:
   a C-shaped support arm;
   an X-ray source contained near one end of the support arm;
   a rechargeable power source internal to the support arm, the power source having a total energy capacity ranging from about 65 Watt-hour to about 170 Watt-hours; and
   an X-ray detector contained near the other end of the support arm.

10. The device of claim 9, wherein the X-ray device is configured to be hand-held.

11. The device of claim 9, wherein the device weighs less than about 20 pounds.

12. The device of claim 9, wherein the power source is a removable battery pack.

13. The device of claim 12, wherein the battery pack is made of a lithium-containing material.

14. The device of claim 13, wherein the battery pack comprises Li-ion or LiFePo batteries.

15. The device of claim 13, wherein the battery pack contains 5 to 7 battery cells in series.

16. The device of claim 15, wherein the individual battery cells have a charge capacity ranging from about 3000 mAh to about 3700 mAh.

17. The device of claim 9, wherein the power source provides an operational time for the portable x-ray device ranging from about 6 hours to about 10 hours before being recharged or replaced.

* * * * *